United States Patent [19]

Faraz et al.

[11] Patent Number: 5,824,007
[45] Date of Patent: Oct. 20, 1998

[54] ADJUSTABLE SURGICAL STAND

[75] Inventors: Ali Faraz, Coquitlam; Shaharam Payandeh, Port Moody, both of Canada

[73] Assignee: Simon Fraser University, Burnaby, Canada

[21] Appl. No.: 758,350

[22] Filed: Dec. 3, 1996

[51] Int. Cl.[6] .................................................. A61B 19/00
[52] U.S. Cl. .......................................... 606/130; 600/102
[58] Field of Search ........................... 606/130, 1; 128/4, 128/6; 600/102, 225, 227

[56] References Cited

U.S. PATENT DOCUMENTS

| | | |
|---|---|---|
| 4,140,226 | 2/1979 | Richter . |
| 4,592,352 | 6/1986 | Patil . |
| 4,638,799 | 1/1987 | Moore . |
| 4,899,730 | 2/1990 | Stennert . |
| 4,943,296 | 7/1990 | Funakubo . |
| 4,975,016 | 12/1990 | Pellenc et al. . |
| 5,047,036 | 9/1991 | Koutrouvelis . |
| 5,078,140 | 1/1992 | Kwoh . |
| 5,086,401 | 2/1992 | Glassman et al. . |
| 5,100,411 | 3/1992 | Koutrouvelis . |
| 5,201,325 | 4/1993 | McEwen et al. . |
| 5,221,283 | 6/1993 | Chang . |
| 5,305,203 | 4/1994 | Raab . |
| 5,308,352 | 5/1994 | Koutrouvelis . |
| 5,368,015 | 11/1994 | Wilk . |
| 5,372,147 | 12/1994 | Lathrop, Jr. et al. . |
| 5,380,338 | 1/1995 | Christian . |
| 5,397,323 | 3/1995 | Taylor et al. . |
| 5,402,801 | 4/1995 | Taylor . |
| 5,417,210 | 5/1995 | Funda et al. . |
| 5,441,505 | 8/1995 | Nakamura . |
| 5,445,166 | 8/1995 | Taylor . |
| 5,571,072 | 11/1996 | Kronner .................................. 600/102 |
| 5,609,565 | 3/1997 | Nakamura ............................... 600/227 |

OTHER PUBLICATIONS

Gregory J. Hamlin and A.C. Sanderson, *A Novel Concentric Multilink Spherical Joint with Parallel Robotics Applications*, 1267–1272.

Faraz et al. *Application of Robotics in Endoscopic Surgery*, Proc. 15th Canadian Congress of Applied Mechanics 28 May—1 Jun. 1995, pp. 252–253.

Faraz et al. *Issues and Design Concepts in Endoscopic Extenders*, Proceedings of the 6th IFAC/IFIP/IFORS/IEA Symposium on Analysis, Design and Evaluation of Man—Machine Systems pp. 109–114.

*Primary Examiner*—Michael Buiz
*Assistant Examiner*—William Lewis
*Attorney, Agent, or Firm*—Oyen Wiggs Green & Mutala

[57] ABSTRACT

A support stand for surgical implements is disclosed. The support stand provides an operating environment which is particularly useful for use in laparoscopic surgery. The support stand is compact and includes positionable wrists for providing spherical motion of surgical implements about fixed points which can be made to coincide with incisions in a patient being operated on. Each wrist includes a member pivotally mounted to a support arm. Rotating the member provides rotation about a first axis passing through a fixed point. A surgical instrument holder is connected to the member by a linkage which provides rotation about a second axis passing through the fixed point. The linkage has four pivotally connected links, two of which are bent through an angle to provide precise spherical rotation about the fixed point.

15 Claims, 6 Drawing Sheets

ADJUSTABLE SURGICAL STAND

FIELD OF THE INVENTION

This invention relates to a stand for assisting a surgeon by holding surgical implements, such as endoscopes, remote manipulators, suturing devices and the like during surgery. The stand has particular application in laparoscopic surgery.

BACKGROUND OF THE INVENTION

Laparoscopic surgery is conducted with the use of specialized medical instruments which enter the field of the operation through small incisions which are typically less than ½" in diameter. This is in contrast to conventional surgery wherein a surgeon makes a large incision to enable direct manipulation of the afflicted area of a patient. Laparoscopic surgery is extremely difficult for a surgeon to learn because it involves moving the ends of surgical implements in complicated three dimensional patterns without a clear view of the operative field.

Some devices have been proposed to hold surgical implements during surgery. In general these devices are cumbersome. Because they extend from a stand adjacent the patient, providing devices to hold two or more surgical implements is not practical because the devices crowd the limited area around the patient.

Jensen, PCT Patent Application No. PCT/US94/04867 discloses a remote center positioner which can be used to support a surgical instrument during laparoscopic surgery. The Jensen device provides a center of spherical rotation which can be placed to coincide with the point of entry of a surgical instrument into a patient's abdomen. The center of rotation is remote from any joints or mechanical supports. A problem with the Jensen device is that it requires some pivot axes of links in the positioner to pass through the center line of the surgical instrument being supported. If the pivot axes are not on the centre line of the surgical instrument then the Jensen mechanism will not function precisely as a spherical joint at the incision point. That is, under some conditions the surgical instrument will translate in one direction or the other at the site of the incision. This is not desirable. Further, the Jensen device is a large bulky device.

Taylor et al., U.S. Pat. No. 5,397,323 shows a robotic system comprising a parallelogram multi-link joint. Once again, the Taylor et al. system permits the tool being held to undergo lateral motion unless the pivot points define axes which pass through the center line of the surgical instrument being held. The Taylor device is also a large bulky device which is designed to be mounted alongside a patient and therefore crowds the limited space available in an operating theater. As a result of the deficiencies described above, neither Jensen nor Taylor et al. describe a linkage for holding a surgical instrument which is ideal for use in either general surgery or laparoscopic surgery.

SUMMARY OF THE INVENTION

A first aspect of this invention provides a stand for holding surgical implements which does not suffer from the limitations outlined above. In particular, the invention provides a surgical support stand comprising: a support arm and a wrist projecting from a distal end of the support arm. The wrist comprises: a member pivotally mounted to the support arm for rotation about a first axis, the first axis passing through a fixed point; a surgical instrument holder for holding an axis of a surgical instrument passing through the fixed point; and, a linkage connecting the surgical instrument holder to the member. The linkage comprises: a first link pivotally mounted to the member at a first pivot point a first distance ($L_3$) from the first axis; a second link pivotally mounted to the member at a second pivot point the first distance from the first axis; a third link pivotally mounted to the surgical instrument holder at a third pivot point the first distance from the axis of the surgical instrument; and, a fourth link pivotally mounted to the surgical instrument holder at a fourth pivot point the first distance from the axis of the surgical instrument. The first and second links are pivotally connected to the third link. The second link is pivotally connected to the fourth link. The second and third links each bend through an angle Φ at their point of pivotal connection.

In a preferred embodiment Φ is in the range of about 10 degrees to about 20 degrees and is most preferably about 14 degrees.

A second aspect of the invention provides a surgical support stand comprising: an arm support member; means for moving the arm support member to a desired elevation; and, at least two arms pivotally attached to the arm support member, each of the arms having a movable distal end bearing a wrist member, each of the wrist members providing remote spherical rotation about a fixed point, each of the wrist members comprising a member affixed to the distal end for pivotal rotation about an axis of rotation depending downwardly at an angle in the range of about 5 degrees to about 45 degrees to the horizontal and intersecting the fixed point.

In a preferred embodiment, each of the arms comprises pivotally connected proximal and distal arm segments and the wrist extends at an angle (α) in the range of about 40 degrees to about 80 degrees to a longitudinal axis of the distal arm segment.

BRIEF DESCRIPTION OF THE DRAWINGS

In drawings which illustrate non-limiting preferred embodiments of the invention.

DETAILED DESCRIPTION OF THE PREFERRED EMBODIMENT

Figure 1:
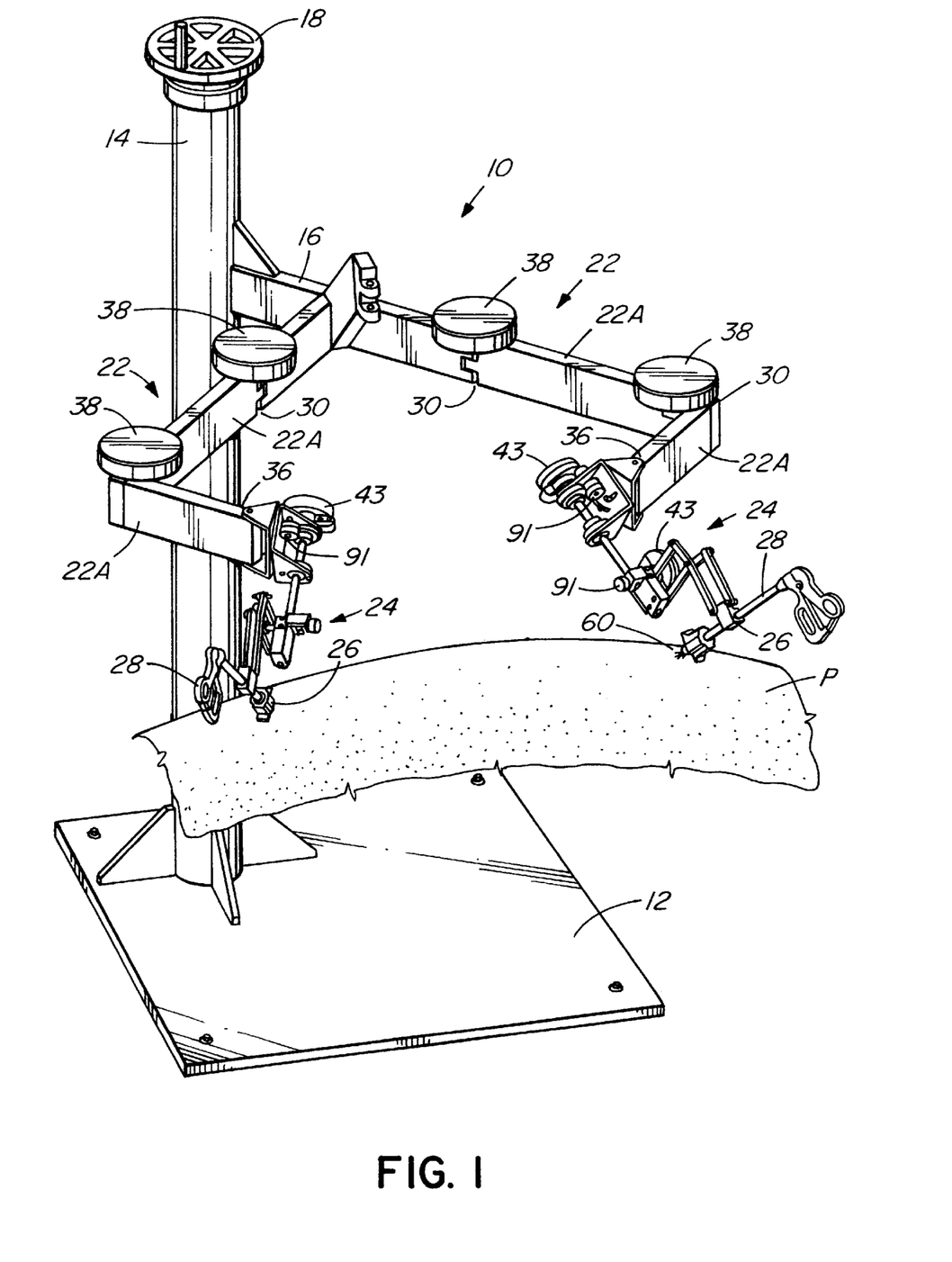
FIG. 1 is a perspective view of a surgical support stand according to the invention.

As shown in FIG. 1, a surgical support stand 10 is used to position surgical instruments in respect of a patient P. Stand 10 has a base 12 which supports a pillar 14. An arm support 16 is slidably attached to pillar 14. Arm support 16 can be moved vertically by means any suitable driving means such as handwheel 18 or a power assisted drive (not shown). These parts of stand 10 allow arm support 10 to be rigidly fixed at a desired elevation by operating handwheel 18. Of course, many variations are possible in the design of this portion of stand 10. For example, pillar 14 could be attached to a wall and not be supported by a base. Arm support 16 could be rigidly fixed to a support member in applications for which vertical adjustment is not required or in which the elevation of the patient P can be adjusted. It is merely necessary that arm support 16 can be held rigidly at a desired elevation in respect to patient P.

Arm support 16 supports at least one, and preferably supports two or more arms 22. Some of the advantages of the invention may be realized in a support stand having only one arm 22. If more than two arms are provided then preferably the third and subsequent arms are supported at a different elevation from the first and second arms so as not to interfere with motion of the first and second arms.

Figure 4A:
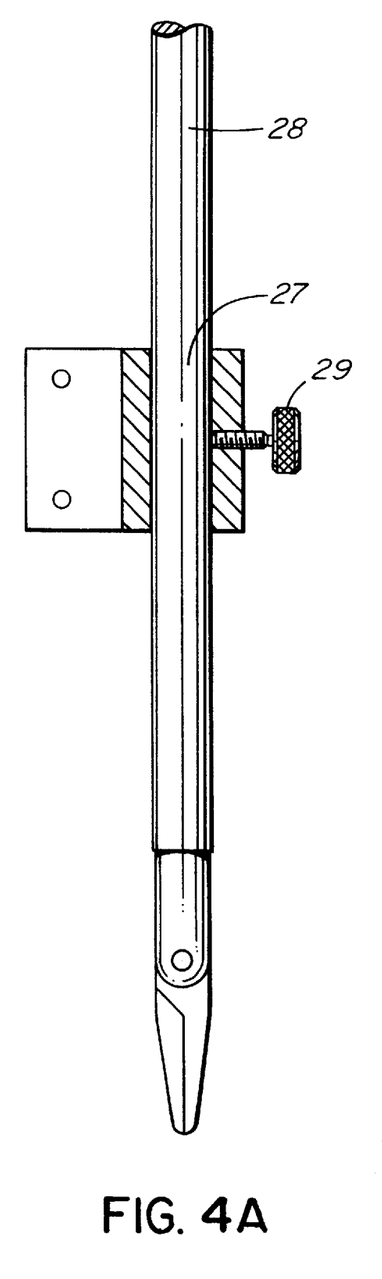
FIGS. 4A and 4B are sections through an implement holder for holding surgical tools for use with the invention; and, FIG. 5 is a top plan schematic view of a surgeon using a stand according to the invention.
Figure 4B:
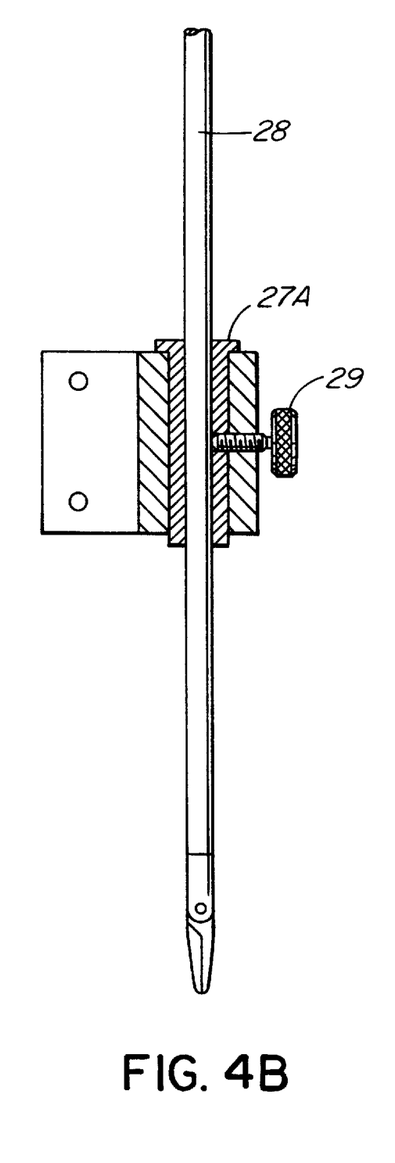

An implement holding wrist 24 is attached at the end 36 of each arm 22. An implement holder 26 is attached at the distal end of each wrist 24. Implement holders 26 are adapted to receive surgical implements 28 such as manipulators, suturing devices, endoscopes, and so on. As shown in FIGS. 4A and 4B, implement holders 26 preferably comprise a cylindrical bore 27 sized to receive the shaft of an implement 28 and a clamp, which may be as simple as a screw 29, to hold implement 28 at a desired position in bore 27. Those skilled in the art will realize that any practical clamping mechanism may be used in place of screw 29 without departing from the scope of the invention. Sleeves 27A may be provided to properly secure implements 28 having shafts with diameters less than the diameter of bore 27.

Arms 22 are each pivotally mounted to arm support 16. Preferably each arm 22 comprises two or more arm segments 22A connected by two or more joints 30 which allow the free distal ends 36 of arms 22 to be moved to position surgical implements anywhere within an operating area above patient P. In typical applications, an operating area of about 500 mm by 350 mm is sufficient. Consequently, in typical applications, each arm should preferably be positionable in an area of at least about 250 mm by 350 mm.

Figure 5:
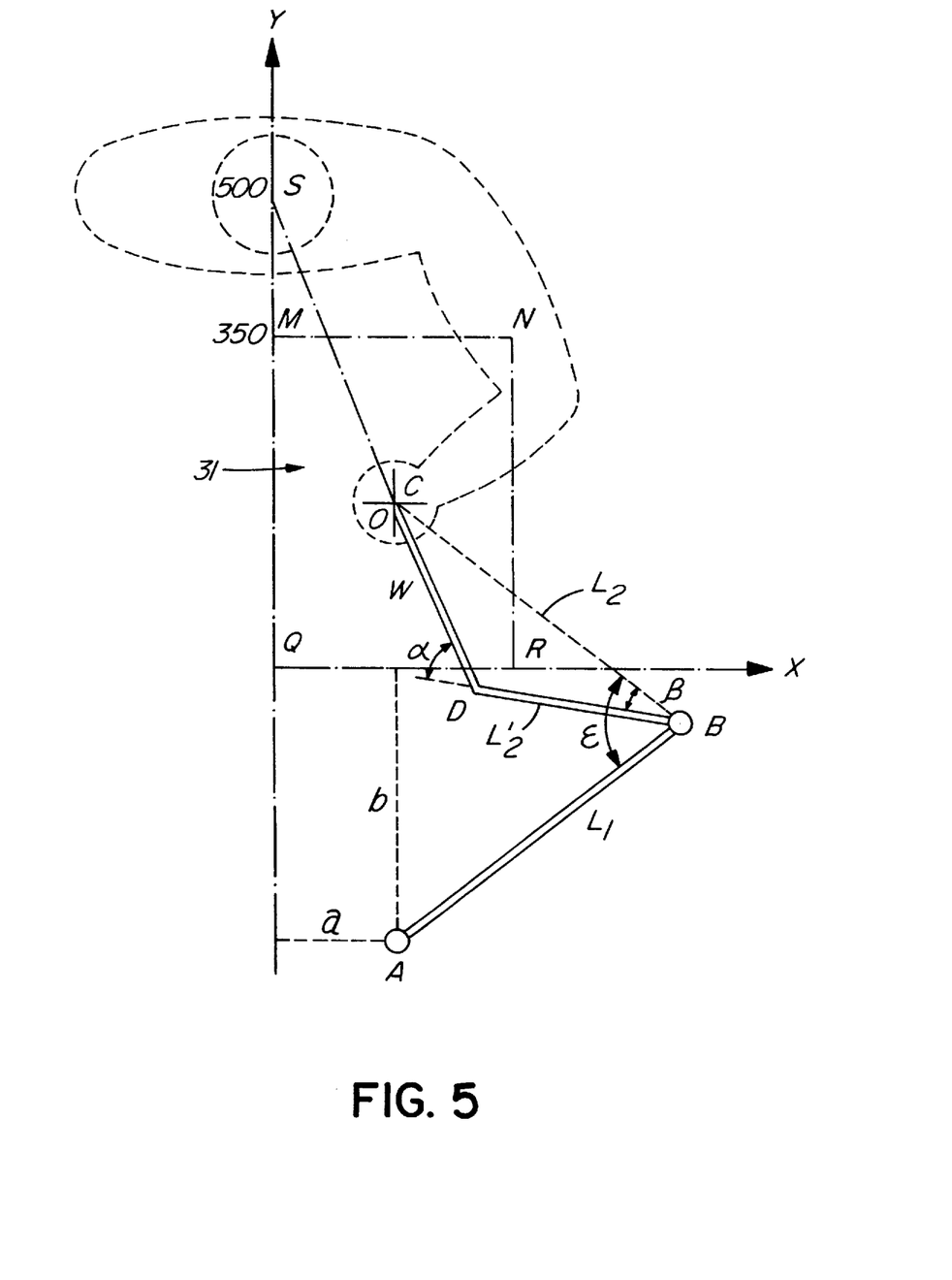

Preferably all of joints 30 pivot about vertical axes so that ends 36 may be positioned as desired in a horizontal plane by bending arms 22 at joints 30. With this construction, the position of arms 22 does not affect the elevation of ends 36 above patient P. Most preferably, wrists 24 always point directly toward the surgeon who is using stand 10. That is, the surgeon, fixed point 60 (i.e. the incision point) and end 36 should preferably all lie on a straight line as shown in FIG. 5 as points S, C, and D respectively. This could be accomplished by providing an additional actuated joint at the end of arm 22 (at point D) with a controller to adjust the angle α between wrist 24 and the end segment of arm 22 so that wrist 24 is always directed toward the position where a surgeon would stand.

In practice, when stand 10 is used as a passive positioning stand, an actuated joint is generally not necessary. The angle α can be fixed so that wrist 24 has the desired orientation when surgical implement 28 is, for example, positioned in the center of the operative area. The inventors have determined that α should be in the range of about 10 degrees to about 80 degrees in most applications and is most preferably in the range of about 40 degrees to about 60 degrees.

Each joint 30 is equipped with locking means such as a pneumatic brake 38. Air pressure can be applied to lock pneumatic brakes 38. When brakes 38 are not locked ends 36 of arms 22 may be freely moved.

Figure 3A:
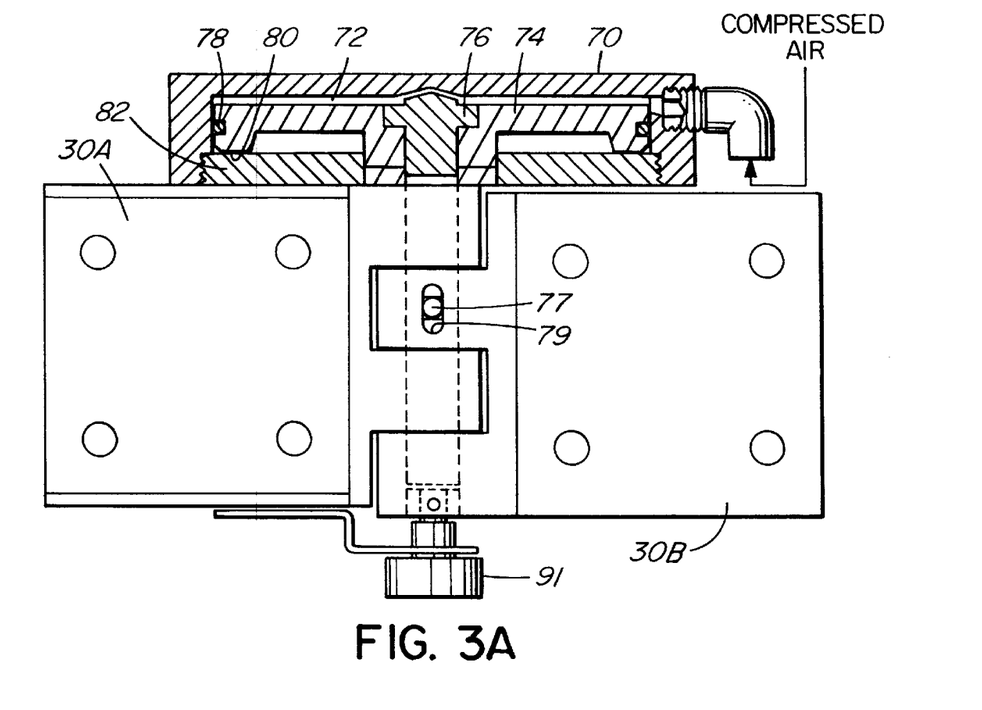
FIGS. 3A and 3B are sections through pneumatic locks for use with the invention.

A preferred construction for a pneumatic brake 38 is shown in FIG. 3A. Pneumatic brake 38 comprises a housing 70 which is attached to a first side 30A of joint 30. Housing 70 has an internal cavity 72 which contains a rotor disc 74. Rotor disc 74 is attached to a hinge shaft 76 which is attached, in turn, to a second side 30B of joint 30 by a pin 77. Pin 77 can move vertically in a slot 79 so that shaft 76 can move longitudinally with rotor disc 74 in response to changes in pressure within cavity 72. Rotor disc 74 has a seal 78 which seals cavity 72. When compressed air is introduced into cavity 72 then rotor disc 74 is driven downwardly so that a friction surface 80 on rotor disc 74 firmly engages a friction member 82 attached to first side 30A of joint 30. When pneumatic brakes 38 are applied then pneumatic brakes 38 hold joints 30 rigidly and prevent ends 36 from moving.

Wrists 24 are attached to project downwardly from the distal ends 36 of arms 22 at angles γ.

In designing arms 22 it is generally desirable to minimize the overall mass of arms 22 so that they are easy to move. In general this means that arms 22 should be kept as short as possible while still permitting surgical implements 28 to be placed anywhere within the operative area and while avoiding configurations of arms 22 in which the angles of joints 30 may make it difficult to change the configuration of arms 22. In practice, where arms 22 comprise two links, as shown, the angle ε between the two links should not approach 0° or 180° when surgical implement 28 is in the operating area. Typically the angle ε between the links should be in the range of about 60° to 135° when surgical implement 28 is in the operating area. The operating area 31 for one arm 22 as shown in FIG. 5 is, for example, 250 mm by 350 mm.

Wrists 24 perform exactly as remote spherical joints. That is, when a surgical instrument 28 is engaged in one of implement holders 26 then wrist 24 does not allow instrument 28 to move relative to a fixed point 60. During surgery fixed point 60 is made coincident with the incision in patient P so that motion of instrument 28 does not stretch or tear the incision.

Figure 2A:
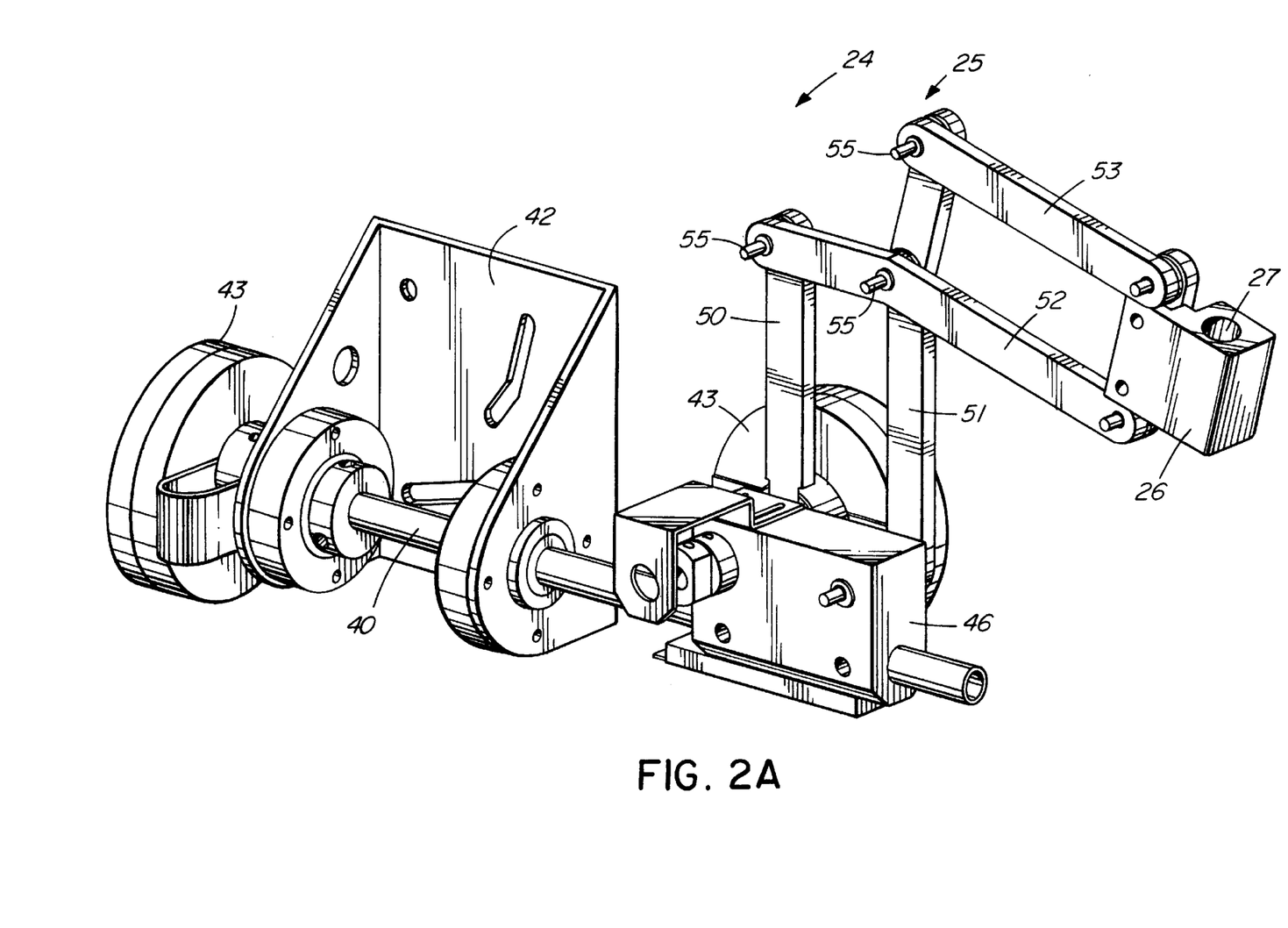
FIG. 2A is a perspective view of a linkage implementing a remote spherical joint for use with the invention.
Figure 3B:
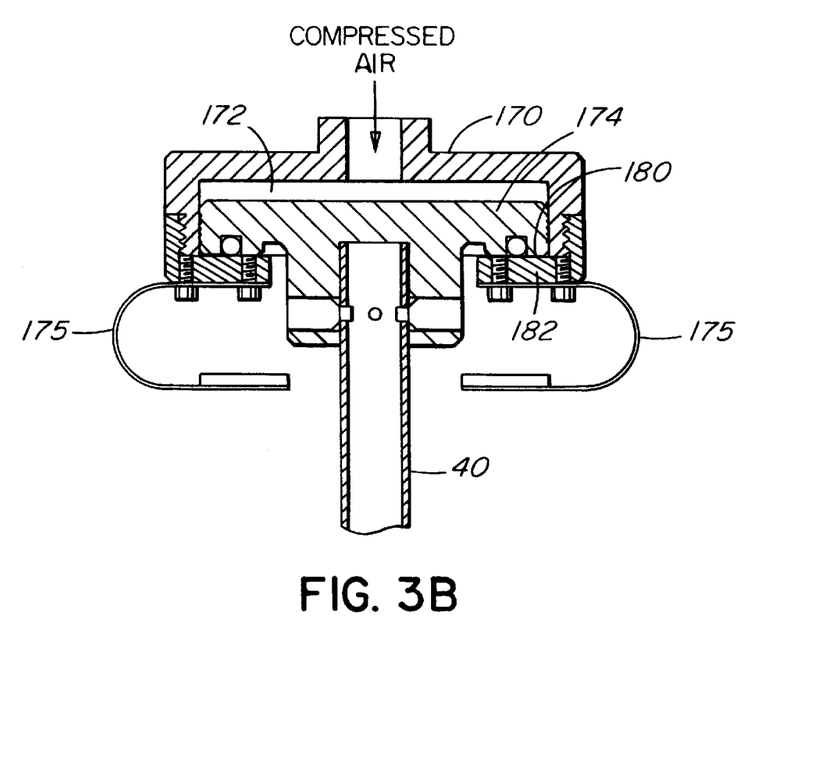

As shown in FIG. 2A, each wrist 24 comprises a member 40 pivotally mounted in a bracket 42 at the end 36 of arm 22. Member 40 is preferably mounted in suitable bearings so that it can be easily and freely rotated about its axis. A locking means such as a pneumatic brake 43 is provided to lock member 40 at a desired angle of rotation about its axis. One end of member 40 projects from bracket 42. The operation of pneumatic brake 43 can be understood with reference to FIG. 3B. Pneumatic brake 43 comprises a housing 170 which is attached to bracket 42 by springs 175. Springs 175 allow housing 170 to move longitudinally of the axis of member 40 but do not permit housing 170 to rotate about the axis of member 40. Housing 170 has an internal cavity 172 which contains a rotor disc 174. Rotor disc 174 is attached to member 40. Rotor disc 174 has a seal 178 which seals cavity 172. When compressed air is introduced into cavity 172 then housing 170 is driven away from bracket 42 so that friction surfaces 180 on rotor disc 174 firmly engage a friction member 182 attached to housing 170. When pneumatic brake 43 is applied then member 40 is prevented from turning about its longitudinal axis.

Figure 2B:
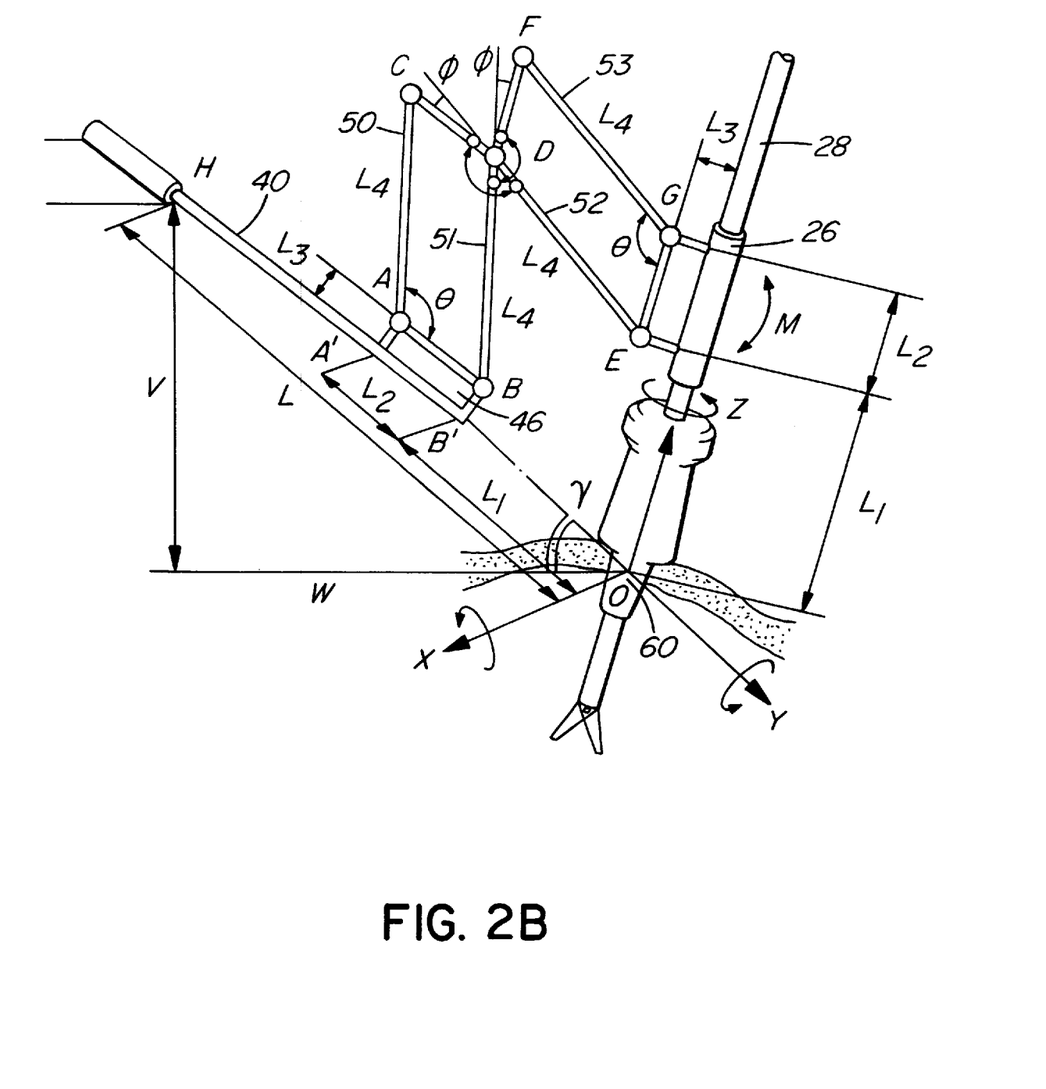
FIG. 2B is a detailed schematic view of a linkage implementing a remote spherical joint for use with the invention.

Implement holder 26 is connected to a mounting 46 at the extreme end of member 40 by a linkage 25 comprising four arms 50, 51, 52 and 53. Arms 50 and 51 are parallel to each other. Arms 52 and 53 are parallel to each other. Arms 51 and 52 are each bent through an angle Φ as shown in FIG. 2B. Arms 50 and 51 are pivotally mounted to mounting 46. Arms 52 and 53 are pivotally mounted to implement holder 26. Arms 50, 51, 52 and 53 are pivotally connected to each other by pivot joints 55.

In FIG. 2B, the individual pivot joints 55 of linkage 25 (which is also shown in FIG. 2A) are identified by the letters A, B, C, D, E, F and G. $L_1$ is the distance along the axis of implement 28 between pivot point E and fixed point 60 and is also the distance along the axis of member 40 between pivot point B and fixed point 60. $L_2$ is the distance between pivot points A and B, which is the same as the distances between the pairs of pivot points C and D, D and F, and E and G. Pivot points A and B are equally spaced from member 40 by a distance $L_3$. Similarly, pivot points E and G are equally spaced from the axis of implement holder 26 by a distance $L_3$. $L_4$ is the distance between pivot points A and C, which is the same as the distance between the pairs of pivot points B and D, D and E, and F and G.

For linkage 25 to function properly and provide a remote center of spherical rotation about point 60 the following constraints should be satisfied:

$$\tan \Phi = L_3/L_1 \quad (1)$$

and $$L_4 = L_3/\sin \Phi \quad (2)$$

Furthermore, to avoid extreme forces on any of pivot joints 55 the ratio $L_4$ to $L_2$ must be limited. If either of $L_2$ or $L_4$ approaches 0 then the force which could theoretically be applied to one of joints 55 approaches infinity. Of course, linkage 25 would fail well before this happened. If it is acceptable for some of pivot joints 55 (e.g. D, E, F, and G) to absorb forces up to twice as large as other pivot joints 55 (e.g. A, B, C) by a surgeon applying forces or torques to implement holder 26 then the following condition should be observed:

$$2 \geq L_4/L_2 \geq \frac{1}{2} \quad (3)$$

It is generally desirable to minimize the overall size of wrist 24 for any particular application so that wrist 24 is not clumsy and obtrusive. One way to minimize the overall size of wrist 24 is to minimize the distance between bracket 42 and fixed point 60 as measured along the axis of member 40. It can be seen that this distance is the sum of the distances from bracket 42 to point A, from point A to point B, and from point B to point 60. To avoid interference between arm 50 and bracket 42, the distances from bracket 42 to point A should be greater than the length of arm 50. It can be seen that the minimum distance from bracket 42 to point 60 along the axis of member 40 can be expressed as follows:

$$\text{Distance} = L_1 + L_2 + L_4 = L_1 + L_2 + L_5/\sin \Phi \quad (4)$$

If, for example, in a given application it is necessary for $L_1$ to be at least 80 mm (e.g. to allow use of a trocar up to about 80 mm long) and $L_3$ is at least 20 mm (e.g. to accommodate the joints being used) then Equation (4) can be solved numerically subject to the constraints set out in Equations (1), (2) and (3) to yield the following solution:

$$L_1 = 80 \text{ mm } L_2 = 41.2 \text{ mm } L_3 = 20 \text{ mm } L_4 = 82.4 \text{ mm } \Phi = 14.0° \quad (5)$$

The overall length of this portion of wrist 24 is 203.7 mm with these dimensions.

In an optimized stand for holding surgical instruments during laparoscopic surgery, $\Phi$ is typically in the range of about 5 degrees to about 45 degrees, is preferably greater than about 10 degrees, and is most preferably about 14 degrees.

The angle $\gamma$ between the axis of member 40 and the horizontal may be fixed or made adjustable. In general, $\gamma$ should be as small as possible to obtain the largest range of angular motion of joints 55 in wrist 24. In practice, $\gamma$ must be large enough so that bracket 42 clears the surface of patient P by a suitable distance of, for example, at least 40–50 mm. In an optimized stand for supporting surgical instruments in laparoscopic surgery, $\gamma$ will typically be in the range of about 5 degrees to about 45 degrees and will most typically be about 15 degrees.

In use, the brakes or "locks" 38 on arms 22 are released and arms 22 are positioned so that the fixed points 60 of wrists 24 coincide with incisions in the patient being operated on. Then locks 38 are applied (for example by applying pressurized gas) to prevent points 60 from moving from the incision points. Surgical implements 28 may then be slid into implement holder 26 and into the body of patient P. Surgical implement 28 can then be manipulated in any of three independent directions by respectively: rotating member 40 about its axis; changing the angle of arms 50 to 53 and implement holder 26 relative to member 40; rotating surgical instrument 28 along its longitudinal axis in holder 26; or inserting or withdrawing surgical implement 28 relative to patient P. Surgical implement 28 can be locked in place in respect of any or all of these four directions of movement.

Stand 10 is well adapted for use as a basis for a robotic surgery device. The position of a surgical implement 28 can be readily monitored by affixing angular position sensors 91 to each of joints 30, member 40, and at least one of the pivot points of linkage 25. Furthermore, motors or other actuators could be connected using known means to drive and control the motion of any or all of the joints in stand 10.

From the foregoing description, those skilled in the art will realize that the surgical stand described above provides an uncluttered surgical environment which is qualitatively very different from that provided by prior art surgical support stands. A support stand, as described, may enable a surgeon to perform surgery with fewer assistants than would be required for the same surgery without such a stand. The stand is functional and yet does not unnecessarily crowd an operating theater. The support stand described above can support multiple surgical implements while the implements are being moved. The implements may be locked in desired positions and orientations. A support stand, as described above, can also provide support for a surgeon's arms during long or complicated surgery.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

What is claimed is:

1. A support stand for holding and allowing remote spherical rotation of a surgical implement about a fixed point, said support comprising:
   (a) a support arm;
   (b) a wrist (24) projecting from a distal end of said support arm (22), said wrist comprising:
      (i) a member (40, 46) pivotally mounted to said support arm for rotation about a first axis, said first axis passing through a fixed point (60);
      (ii) a surgical instrument holder (26) for holding an axis of a surgical instrument (28) passing through said fixed point; and,
      (iii) a linkage (25) connecting said surgical instrument holder to said member, said linkage comprising:
         (1) a first link (50) pivotally mounted to said member (40, 46) at a first pivot point (A) a first distance ($L_3$) from said first axis;

(2) a second link (51) pivotally mounted to said member (40, 46) at a second pivot point (B) said first distance from said first axis;

(3) a third link (52) pivotally mounted to said surgical instrument holder at a third pivot point (E) said first distance from said axis of said surgical instrument; and, (4) a fourth link (53) pivotally mounted to said surgical instrument holder at a fourth pivot point (G) said first distance from said axis of said surgical instrument;

wherein said first and second links are pivotally connected to said third link, said second link is pivotally connected to said fourth link and said second and third links each bend through an angle Φ at their point of pivotal connection to each other.

2. The support stand of claim 1 wherein said distal end of said support arm is movable in a horizontal plane and said support stand comprises a lock for fixing said distal end at a desired location.

3. The support stand of claim 2 wherein said member (40) depends from said arm at an angle (γ) in the range of about 5 degrees to about 45 degrees to the horizontal.

4. The support of claim 3 wherein said angle γ is approximately 15 degrees.

5. The support stand of claim 3 wherein said arm comprises a plurality of arm segments pivotally connected to each other by joints having vertical pivot axes.

6. The support stand of claim 5 wherein said arm comprises first and second arm segments and said wrist extends at an angle (α) in the range of about 10 degrees to about 80 degrees to a longitudinal axis of said second arm segment.

7. The support stand of claim 6 comprising an actuator for setting said angle α and a controller operatively connected to said actuator for adjusting said angle α so that said first axis of said member always intersects a chosen vertical line.

8. The support stand of claim 7 wherein said angle Φ is in the range of about 10 degrees to about 20 degrees.

9. The support stand of claim 3 comprising two or more support arms (22) mounted to a common arm support (16), each of said support arms having a wrist (24) projecting from a distal end of said support arm (22), said wrist comprising:

(i) a member (40, 46) pivotally mounted to said support arm for rotation about a first axis, said first axis passing through a fixed point (60);

(ii) a surgical instrument holder (26) for holding an axis of a surgical instrument (28) passing through said fixed point; and, (iii) a linkage (25) connecting said surgical instrument holder to said member, said linkage comprising:

(1) a first link (50) pivotally mounted to said member (40, 46) at a first pivot point (A) a first distance ($L_3$) from said first axis;

(2) a second link (51) pivotally mounted to said member (40, 46) at a second pivot point (B) said first distance from said first axis;

(3) a third link (52) pivotally mounted to said surgical instrument holder at a third pivot point (E) said first distance from said axis of said surgical instrument; and, (4) a fourth link (53) pivotally mounted to said surgical instrument holder at a fourth pivot point (G) said first distance from said axis of said surgical instrument;

wherein said first and second links are pivotally connected to said third link, said second link is pivotally connected to said fourth link and said second and third links each bend through an angle Φ at their point of pivotal connection to each other.

10. The support stand of claim 9 wherein said angle Φ is in the range of about 10 degrees to about 20 degrees.

11. The support stand of claim 2 comprising a first powered locking means for releasably locking rotation of said member about said first axis.

12. The support stand of claim 11 comprising a second powered locking means for releasably locking rotation of said first link relative to said member.

13. The support stand of claim 11 wherein said first locking means comprises a resilient member affixed to said arm, a housing affixed to said resilient member, a rotor in a cavity in said housing, said rotor affixed to said member, and means for introducing a compressed gas or fluid into said cavity to displace said housing into frictional engagement with said rotor.

14. The support stand of claim 1 wherein said angle Φ is in the range of about 5 degrees to about 45 degrees.

15. The support stand of claim 14 wherein said angle Φ is in the range of about 10 degrees to about 20 degrees.

* * * * *